United States Patent
Shi et al.

(10) Patent No.: US 9,814,569 B2
(45) Date of Patent: Nov. 14, 2017

(54) FLEXIBLE VALVE STRUCTURE FOR IMPLANTABLE RESERVOIR

(71) Applicants: Wendian Shi, Monrovia, CA (US); Charles DeBoer, Sierra Madre, CA (US); Sean Caffey, Pasadena, CA (US); Mark S. Humayun, Glendale, CA (US); Yu-Chong Tai, Pasadena, CA (US)

(72) Inventors: Wendian Shi, Monrovia, CA (US); Charles DeBoer, Sierra Madre, CA (US); Sean Caffey, Pasadena, CA (US); Mark S. Humayun, Glendale, CA (US); Yu-Chong Tai, Pasadena, CA (US)

(73) Assignee: ICO, INC., Pasadena, CA (US)

( * ) Notice: Subject to any disclaimer, the term of this patent is extended or adjusted under 35 U.S.C. 154(b) by 0 days.

(21) Appl. No.: 14/980,116

(22) Filed: Dec. 28, 2015

(65) Prior Publication Data
US 2016/0184090 A1    Jun. 30, 2016

Related U.S. Application Data

(60) Provisional application No. 62/097,303, filed on Dec. 29, 2014.

(51) Int. Cl.
| | | |
|---|---|---|
| *A61F 2/16* | (2006.01) | |
| *A61M 39/24* | (2006.01) | |
| *A61M 39/02* | (2006.01) | |
| *A61M 5/142* | (2006.01) | |
| *A61M 39/00* | (2006.01) | |

(52) U.S. Cl.
CPC ....... *A61F 2/1635* (2013.01); *A61M 5/14276* (2013.01); *A61M 39/0208* (2013.01); *A61M 39/24* (2013.01); *A61F 2250/0003* (2013.01); *A61F 2250/0068* (2013.01); *A61M 2039/0036* (2013.01); *A61M 2039/2433* (2013.01)

(58) Field of Classification Search
USPC .................................... 623/6.13, 6.18, 6.59
See application file for complete search history.

(56) References Cited

U.S. PATENT DOCUMENTS

| | | |
|---|---|---|
| 5,091,121 A | 2/1992 | Nakada et al. |
| 2012/0310343 A1 | 12/2012 | Van Noy |
| 2013/0053954 A1 | 2/2013 | Rao et al. |
| 2013/0150960 A1 | 6/2013 | DeBoer et al. |
| 2014/0358155 A1 | 12/2014 | DeBoer et al. |

OTHER PUBLICATIONS

International Search Report and Written Opinion issued in a corresponding International Application No. PCT/US2015/067604 dated Apr. 14, 2016.

*Primary Examiner* — David H Willse
*Assistant Examiner* — Javier Blanco
(74) *Attorney, Agent, or Firm* — Morgan, Lewis & Bockius LLP

(57) ABSTRACT

In various embodiments, implants including reservoirs, such as intraocular lenses, feature flexible membranes and valves integrated therewith, the valves having apertures that are normally closed.

12 Claims, 9 Drawing Sheets

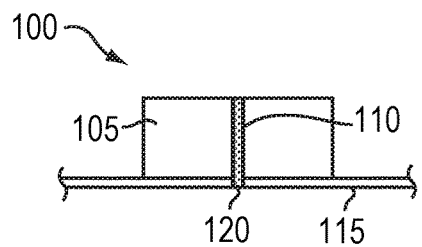
FIG. 1A
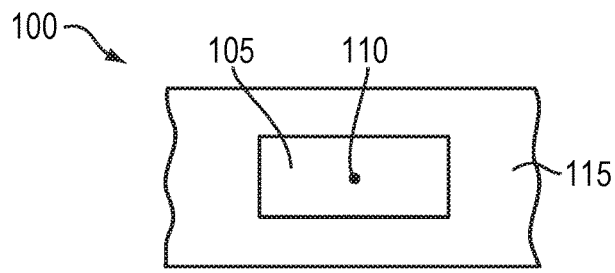
FIG. 1B
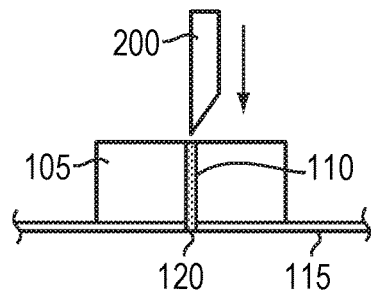 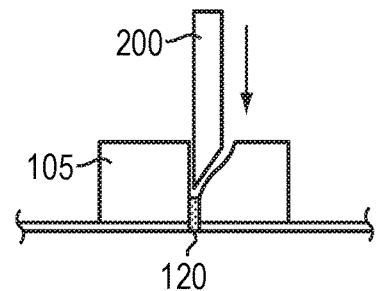
FIG. 2A          FIG. 2B
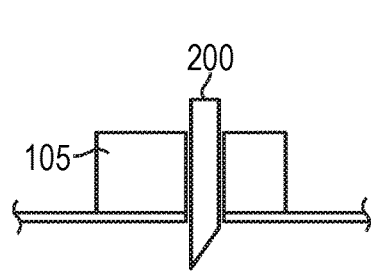 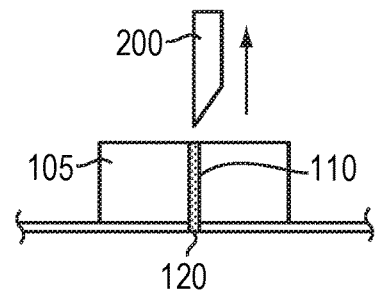
FIG. 2C          FIG. 2D

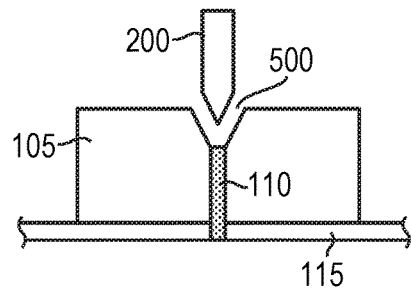
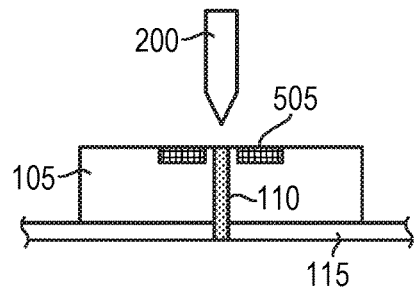
FIG. 5A  FIG. 5B
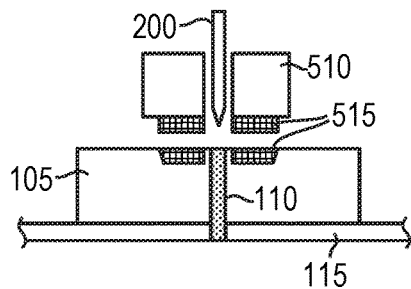
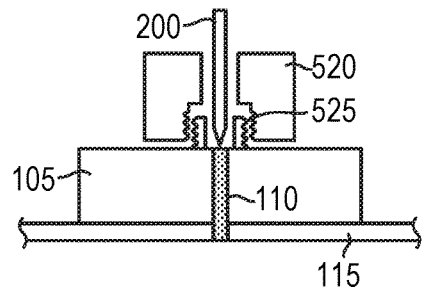
FIG. 5C  FIG. 5D
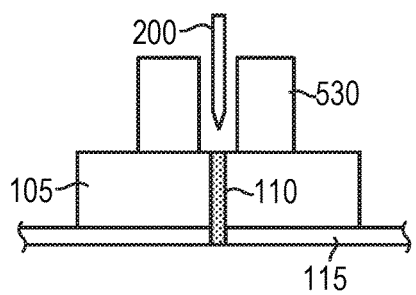
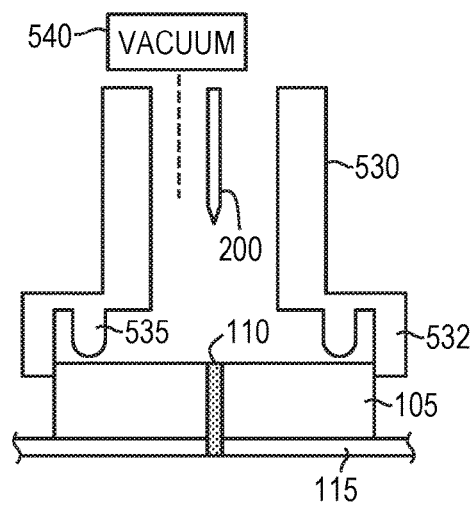
FIG. 5E  FIG. 5F

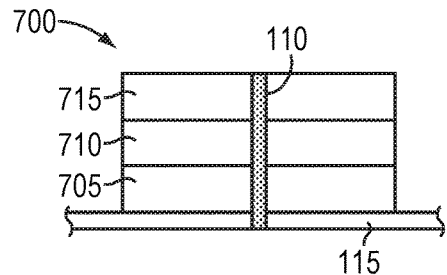
FIG. 7A
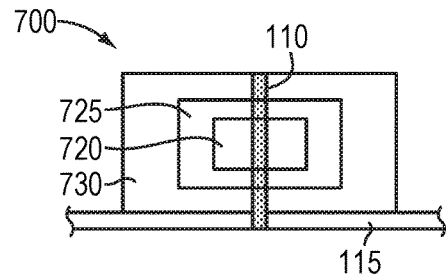
FIG. 7B
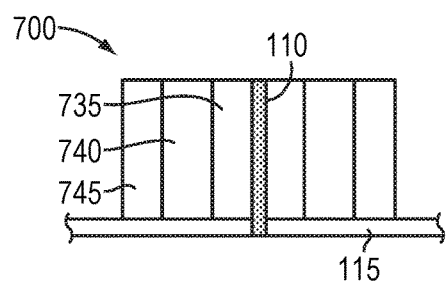
FIG. 7C
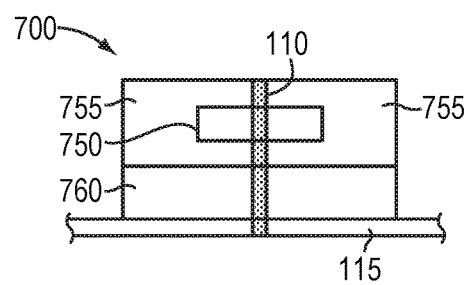
FIG. 7D
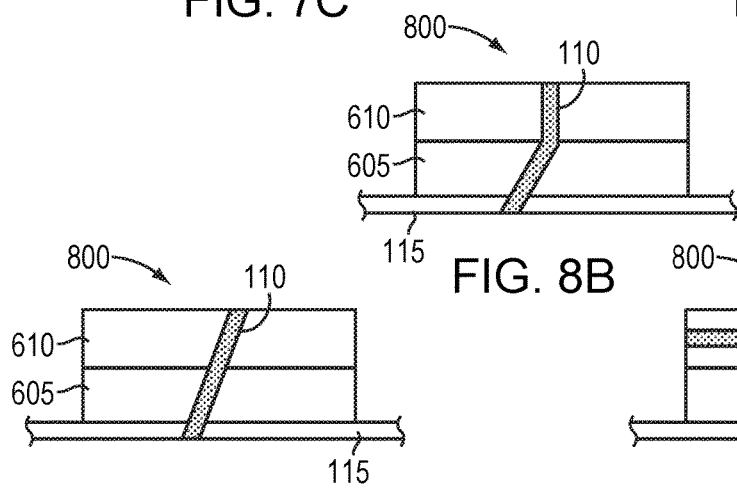
FIG. 8A
FIG. 8B
FIG. 8C
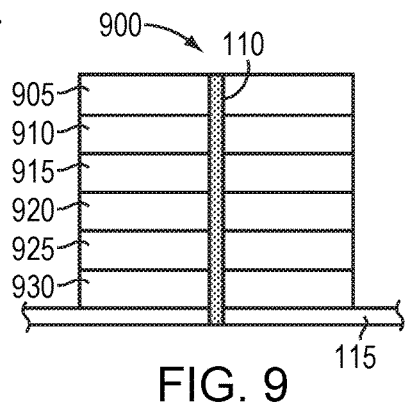
FIG. 9

FLEXIBLE VALVE STRUCTURE FOR IMPLANTABLE RESERVOIR

RELATED APPLICATION

This application claims the benefit of and priority to U.S. Provisional Patent Application No. 62/097,303, filed Dec. 29, 2014, the entire disclosure of which is hereby incorporated herein by reference.

TECHNICAL FIELD

In various embodiments, the present invention relates generally to valves for implantable devices that include a fluid reservoir.

BACKGROUND

Medical procedures at times involve implantation of liquid-filled devices in any of numerous portions of a patient's body. Some examples of fluid-filled reservoirs include breast implants, testicular implants, drug-delivery systems, and adjustable gastric bands. In addition, recently there has been much work involving liquid-filled intraocular lenses. These lenses have the advantage that they can be implanted in an unfilled configuration through a small surgical incision; after implantation, the lens can be inflated. Various intraocular lenses may even use a liquid to change the refractive power of the lens or to interact with the natural eye muscles to focus.

In many liquid-filled devices there is a need for a valve that allows access to the internal contents of the implant. In the case of breast implants, the fluid level can be adjusted to change the size of the implant. In intraocular lenses, the amount or type of fluid in the intraocular lens can change its refractive power or how it interacts with the eye. Often, fluidic access to the reservoir of the liquid-filled device is desired not only during implantation but also afterwards, thereby allowing the implant to be filled, emptied, and/or adjusted. Valve leakage is a particular risk in adjustable liquid-filled devices, because leakage from the implant changes the implant properties and can harm the patient. For example, a breast or testicular implant could change size, a drug reservoir may release a pharmaceutical agent into the body, and a gastric sleeve could change the amount of compression applied to the stomach. Leakage from an intraocular lens may cause refractive error or drift, and/or it may result in less interaction with the eye and decreased accommodation.

Accordingly, there is a need for valves compatible with implantable devices and which resist leakage during ordinary use and following fluidic access to the reservoir, both during and after implantation.

SUMMARY

Many valves currently available are convoluted structures with multiple components that limit the miniaturization of the valve. Additionally, certain valve components are typically rigid, which limits the ability to fold the valve during implantation in order to minimize incision size. For example, most implant valves utilize rigid flange components to reinforce the connection region between the valve and the implant. In various embodiments, the present invention overcomes this shortcoming by avoiding or minimizing the use of rigid valve components, thereby minimizing stress points at the valve connection. Certain embodiments of the invention incorporate sufficient flexibility to at least partially wrap around an insertion needle during implantation.

In various embodiments, the present invention relates to a valve for an implantable reservoir (i.e., a reservoir for or constituting an implant such as a drug-delivery pump or device) and featuring one or more components to aid in sealing the valve. As utilized herein, an implant "including" a reservoir means that the implant can contain the reservoir or can be the reservoir itself. When utilized with an implantable reservoir, the valve substantially prevents leakage of the internal contents of the reservoir to the surrounding tissue and substantially prevents the intrusion of bodily fluid into the reservoir. When the valve is accessed, the valve affords fluidic continuity with the internal fluidic system of the implantable reservoir. Fluidic continuity may be directly to the reservoir, or may be indirect through fluidic channels, a sub-chamber, or other fluidic pathways known to those skilled in the art. In embodiments in which fluidic continuity is indirect via additional fluidic channels, sub-chambers, or any length of fluidic path, one or more of the flexible valves described herein may be incorporated along the pathway with apertures opening by specific orientation of the reservoir or when a specific fluid pressure is exceeded.

Valves in accordance with embodiments of the present invention may have a single valve layer or multiple valve layers. The use of multiple layers may simplify manufacture of the device, allowing, for example, the use of an overmolding process that improves sealing capabilities. In addition, multiple-layer valves allow one component of the valve to serve as a structural support while other portions of the valve act to seal the device. In various embodiments, a valve may have features that simplify use on flexible and/or curved surfaces and further promote foldability; these may include, for example, tapered valve sides, orientations that are in-line with the wall, flexible, tapered stress reliefs, etc.

In one embodiment, a flexible valve integrated in an implantable reservoir includes one or more polymeric layers and a preformed slit that passes through one or more (or even all of) of the layers. The polymeric layers may include, consist essentially of, or consist of different materials, and may have the same or different shapes. The polymeric layers may be disposed in a linear fashion layered on top of one another.

In some embodiments, one or more of the polymeric layers serves to encapsulate the other layers, and the preformed slit passes through at least one of the encapsulated layers. One or more of the encapsulated layers of the valve may include, consist essentially of, or consist of a liquid, gel, or gas and the encapsulating component or components may be solid materials. Various ones of the polymeric layers may have different polarities from one another and thereby act as diffusion barriers.

Typically the pre-formed slit of the valve is normally closed and cracked open, for example, upon application of mechanical pressure from a non-coring needle. The pre-formed slit may be straight, angled, curved, or bent, and as the slit passes through different polymeric layers, it may have different shapes and/or different orientations. The slit may pass through one or more central layers and one or more surrounding layers and wrap around the central layer(s); the surrounding layer(s) may have different mechanical properties from the central layer(s).

The encapsulated area of some valve embodiments may store a pharmaceutical agent (or simply "pharmaceutical") for extended delivery. The pharmaceutical may fill a portion of the encapsulated layer or may reside in a matrix with the encapsulated layer. In some embodiments, the fillable reservoir is at least a portion of an intraocular lens, and the pharmaceutical is an anti-infective and/or a steroid for treatment after the initial surgical procedure.

In an aspect, embodiments of the invention feature an implant including a reservoir configured to receive a filling fluid and expand in response thereto. The reservoir includes or consists essentially of a flexible membrane defining an interior volume and a valve integrated with the membrane. The valve includes, consists essentially of, or consists of (i) a plurality of contiguous polymeric segments and (ii) an aperture extending through at least one of the segments and into the interior volume. The aperture is normally closed to prevent fluid flow therethrough but is openable in response to applied pressure. At least one of the segments has a physical and/or chemical property affecting self-sealing of the aperture that differs from that of at least one of the other contiguous segments.

Embodiments of the invention may include one or more of the following in any of a variety of combinations. The aperture may extend through each of the segments. A first portion of the aperture may extend along a first direction through one of the segments. A second portion of the aperture may extend along a second direction through another one of the segments, the second direction being different from the first direction. At least two of the segments may have different hardnesses. At least two of the segments may include, consist essentially of, or consist of different materials and/or have different levels of cross-linking. A first one of the segments may surround and encapsulate a second one of the segments. The aperture may extend through both the first and second ones of the segments. The second one of the segments may be adapted to receive a pharmaceutical agent. A pharmaceutical agent may be disposed within the second one of the segments. At least two of the segments may have different polarities. The at least two of the segments may function as a diffusion barrier. At least one of the segments may be flexible and at least another one of the layers may be rigid. The membrane may define an intraocular lens implantable in a human eye.

In another aspect, embodiments of the invention feature an implant including a reservoir configured to receive a filling fluid and expand in response thereto. The reservoir includes or consists essentially of a flexible membrane defining an interior volume, a valve integrated with the membrane, and a ring extending at least partially around the valve, whereby pressure applied by the ring closes the aperture. The valve includes, consists essentially of, or consists of (i) one or more contiguous polymeric segments and (ii) an aperture extending through at least one of the segments and into the interior volume. The aperture is normally closed to prevent fluid flow therethrough but is openable in response to applied pressure. The ring may include, consist essentially of, or consist of two or more discontinuous portions having gaps therebetween. The ring may be offset vertically away from a center of a thickness of the valve.

In yet another aspect, embodiments of the invention feature an implant including a reservoir configured to receive a filling fluid and expand in response thereto. The reservoir includes or consists essentially of a flexible membrane defining an interior volume and a valve integrated with the membrane. The valve includes, consists essentially of, or consists of (i) one or more contiguous polymeric segments and (ii) an aperture extending through at least one of the segments and into the interior volume. The aperture is normally closed to prevent fluid flow therethrough but is openable in response to applied pressure. At least a portion of the valve is disposed within the interior volume.

Embodiments of the invention may include one or more of the following in any of a variety of combinations. The entire valve may be disposed within the interior volume. At least one of the segments may be disposed within the interior volume and include a pharmaceutical agent therewithin (or be adapted to receive a pharmaceutical agent therewithin). A first portion of the valve may be disposed outside of the interior volume. A second portion of the valve may be disposed within the interior volume. A hardness of the first portion of the valve may be greater than a hardness of the second portion of the valve. A diameter (or other lateral dimension such as a width) of the first portion of the valve may be greater than a diameter (or other lateral dimension such as a width) of the second portion of the valve. The aperture may extend through the first portion of the valve. The second portion of the valve may define a normally open tunnel fluidly connected to the aperture.

In another aspect, embodiments of the invention feature a combination that includes, consists essentially of, or consists of an implant including a reservoir configured to receive a filling fluid and expand in response thereto and a filling device. The reservoir includes, consists essentially of, or consists of a flexible membrane defining an interior volume, and a valve integrated with the membrane. The valve includes, consists essentially of, or consists of (i) one or more contiguous polymeric segments, an aperture extending through at least one of the segments and into the interior volume, and a needle-guide feature. The aperture is normally closed to prevent fluid flow therethrough but is openable in response to applied pressure. The needle-guide feature is disposed in or on a top surface of the valve proximate the aperture. The filling device has a terminal end in the form of a tube defining a lumen opening at an end face of the terminal end of the filling device and a retractable needle within the lumen. The end face includes a feature configured to mate with the needle-guide feature so as to retain the end face of the terminal end of the filling device against the implantable reservoir with the needle in aligned relation to the aperture.

Embodiments of the invention may include one or more of the following in any of a variety of combinations. The end face of the terminal end of the filling device may be retained against the implantable reservoir during insertion of the needle through the aperture. The needle-guide feature may be a perimeter of the valve and the end face feature may be the lumen. The lumen may be sized to fit snugly over the valve perimeter. The combination may include means for applying a vacuum through the lumen. The needle-guide structure may include, consist essentially of, or consist of a magnetic region having a first polarity. The end face feature may include, consist essentially of, or consist of a second magnetic region having a second polarity opposite the first polarity. The needle-guide structure may include, consist essentially of, or consist of a first locking member. The end face feature may include, consist essentially of, or consist of a second locking member removably matable with the first locking member.

In yet another aspect, embodiments of the invention feature a method of fabricating a reservoir for an implant, where the reservoir is configured to receive a filling fluid and expand in response thereto. A flexible polymeric valve is disposed within a mold. The valve includes, consists essentially of, or consists of (i) at least one polymeric layer, and (ii) an aperture extending through the at least one layer. An interior surface of the mold and at least a portion of the valve are coated with an uncured polymeric material. The polymeric material is at least partially cured, thereby forming a flexible membrane with the valve affixed thereto.

These and other objects, along with advantages and features of the present invention herein disclosed, will become more apparent through reference to the following description, the accompanying drawings, and the claims. Furthermore, it is to be understood that the features of the various embodiments described herein are not mutually exclusive and may exist in various combinations and permutations. As used herein, the terms "approximately" and "substantially" mean±10%, and in some embodiments, ±5%. The term "consists essentially of" means excluding other materials that contribute to function, unless otherwise defined herein. Nonetheless, such other materials may be present, collectively or individually, in trace amounts.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention. In the following description, various embodiments of the present invention are described with reference to the following drawings, in which:

FIG. 1A is a cross-sectional view of a self-sealing valve for an implantable reservoir in accordance with various embodiments of the invention;

FIG. 1B is a top view of the valve of FIG. 1A;

FIGS. 2A-2D schematically illustrate the operation of a self-sealing valve in accordance with various embodiments of the invention;

FIGS. 5A-5F are schematic illustrations of valves incorporating needle-guide structures in accordance with various embodiments of the invention;

FIGS. 7A-7D are schematic cross-sectional views of multi-portion valves in accordance with various embodiments of the invention;

FIG. 8A is a schematic cross-sectional view of a multi-portion valve having an angled aperture in accordance with various embodiments of the invention;

FIGS. 8B and 8C are schematic cross-sectional views of multi-portion valves having non-linear apertures in accordance with various embodiments of the invention;

FIG. 9 is a schematic cross-sectional view of a multi-portion valve in accordance with various embodiments of the invention;

DETAILED DESCRIPTION

Self-Sealing Valve Structure

Figure 3A:
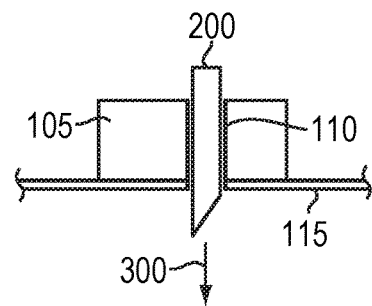
FIGS. 3A and 3B schematically illustrate the introduction and withdrawal of a fluid through a self-sealing valve in accordance with various embodiments of the invention.

With reference to FIGS. 1A and 1B, a valve 100 in accordance with embodiments of the present invention includes a valve body 105 and a self-sealing aperture 110 extending through the valve body 105. The valve 100 is attached to or formed atop a membrane an implantable reservoir 115 and controls access to the contents therein. Only the membrane 115 of the reservoir is shown in FIGS. 1A and 1B; the reservoir typically includes or consists essentially of a sealable volume for containing a fluid such as a pharmaceutical and/or a filling fluid utilized to at least partially control the shape of the reservoir. The aperture 110 may include or consist essentially of, for example, a slit or bore formed through the valve body 105. In various embodiments of the invention, the aperture 110 is normally closed; i.e., the aperture 110 has a sufficiently small diameter or other lateral dimension such that the valve body 105 itself deforms to close the aperture 110, even in the absence of applied force or stress. The closing force may be a result of, for example, residual stress within valve body 105 resulting from the manufacture thereof.

The valve body 105 (or at least a portion (e.g., one or more contiguous segments) thereof) may include, consist essentially of, or consist of, for example, silicone. More generally, however, the valve body 105 may be made from any material (e.g., soft plastic) that that can be punctured with a tool such as a needle and that is capable of re-sealing itself upon removal of the tool. Moreover, the self-sealing material of the valve body 105 may be able to withstand multiple punctures by the tool, and may be biocompatible. In addition to silicone, materials from which the valve body 105 may be manufactured include, but are not limited to, polydimethylsiloxane ("PDMS"), parylene C, parylene HT, polycarbonates, polyolefins, polyurethanes, copolymers of acrylonitrile, copolymers of polyvinyl chloride, polyamides, polysulphones, polystyrenes, polyvinyl fluorides, polyvinyl alcohols, polyvinyl esters, polyvinyl butyrate, polyvinyl acetate, polyvinylidene chlorides, polyvinylidene fluorides, polyimides, polyisoprene, polyisobutylene, polybutadiene, polyethylene, polyethers, polytetrafluoroethylene, polychloroethers, polymethylmethacrylate, polybutylmethacrylate, polyvinyl acetate, nylons, cellulose, gelatin, and porous rubbers. All or a portion of the valve body 105 may be flexible (i.e., elastomeric).

Figure 3B:
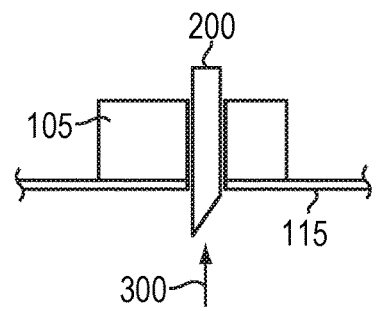

A working principle of valve 100 is illustrated in FIGS. 2A-2D. As shown, underneath the self-sealing aperture 110 of the valve 100, there is an aperture 120 in the implantable reservoir 115. To access the reservoir 115, a needle 200 or other suitable tool is inserted through the valve 100, and the valve body 105 deforms to accommodate, as shown in FIG. 2B. The deformation may result from the use of soft valve materials, plastic deformation of the valve body, etc. As shown in FIG. 2C, when the needle 200 penetrates the entirety of the aperture 110 of the valve body 105, it reaches the aperture 120 of the reservoir 115. As shown in FIG. 2C, the needle 200 then penetrates through the aperture 120 and achieves fluid communication with the content of the reservoir 115. When the needle is removed, as shown in FIG. 2D, the valve body 105 recovers to its original shape and seals. The recovery of shape may result, for example, from the use of soft valve materials, plastic deformation of the valve body, etc. When the valve 100 is opened, the inserted tool (e.g., needle 200) may inject fluid 300 or other contents into the reservoir 115 and remove fluid 300 or other contents from the reservoir, as shown in FIGS. 3A and 3B.

Although the needle 200 is depicted as having a sharp tip or point, in various embodiments the needle 200 is blunt (e.g., having a squared off or curved tip) but capable of opening a pre-formed aperture 110 in the valve. A blunt needle will typically not damage the valve upon insertion, but will instead merely open the normally closed self-sealing pre-formed aperture 110.

Figure 4A:
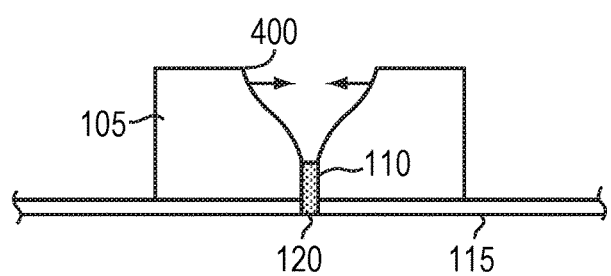
FIGS. 4A-4C schematically illustrate sealing of valves in accordance with various embodiments of the invention.

When the aperture of the valve 100 is closed, its self-sealing behavior assists in closing the valve 100 and preventing leakage from the reservoir 115. Such leakage prevention may be particularly important for applications in which the contents of the reservoir 115 include liquid or other small-molecule contents, and for applications in which a pressure difference exists between the inside of the reservoir 115 and the outside environment. Self-sealing behavior may be achieved in various ways. As illustrated in FIG. 4A, self-sealing may be accomplished by a mechanical closing force originating from elastic deformation of the valve body 105, forcing the sidewall 400 of the aperture 110 to constrict after being forced open (via, e.g., insertion of needle 200 or another instrument). This closing force may be enhanced by inducing preloaded axial compression to the valve 100 during manufacture, e.g., by pre-heating the valve body 105 prior to forming the aperture 110; the aperture may be formed, e.g., by cutting or piercing the body 105 with a blade or other incision instrument, or in any other manner known to those skilled in the art. Alternatively, the aperture in the valve may be created when the valve is first accessed (e.g., when loading the valve into an introducer surgical tool). The self-sealing valve 100 is initially fully closed. Following insertion and removal of a tool through the valve 100, the aperture 110 returns to its closed state via elastic deformation, as shown in FIG. 4A.

Figure 4B:
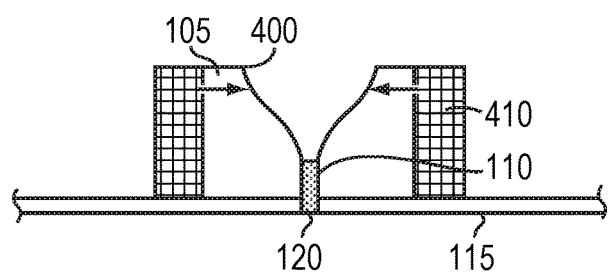
Figure 4C:
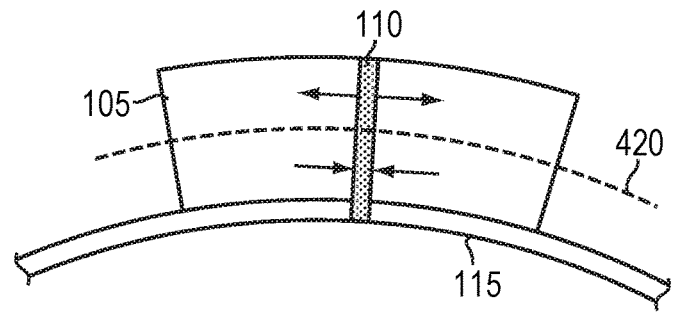
Figure 4D:
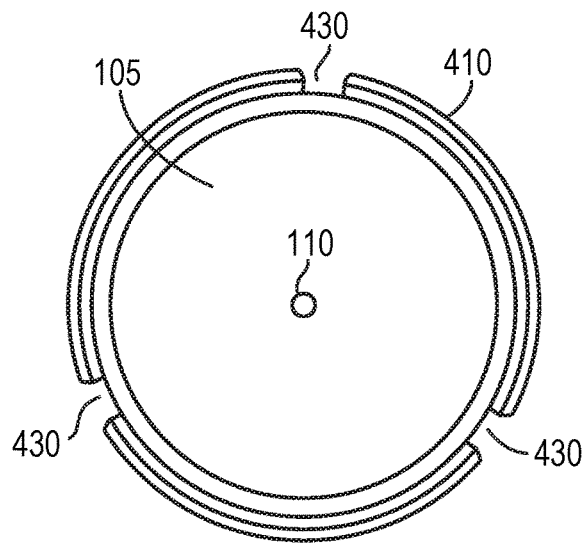
FIG. 4D is a schematic top view of a valve incorporating a partial ring structure in accordance with various embodiments of the invention.
Figure 4E:
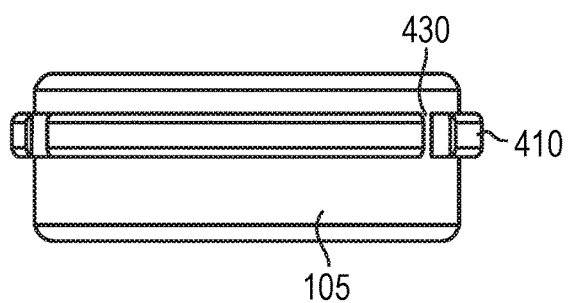
FIG. 4E is a cross-sectional view of the valve of FIG. 4D.

As shown in FIG. 4B, self-sealing may also be accomplished by an external force applied to the valve body 105. For example, as shown, a rigid ring 410 may fully or partially enclose the valve body 105. When the ring 410 is in a loose state (i.e., not compressing valve body 105), the valve aperture 110 may be opened via insertion of a tool such as needle 200. Tightening the ring 410 applies a compressive mechanical force to the valve body 105 and seals the valve aperture 110. The ring 410 may include or consist of, for example, a c-ring, c-clamp, or other open-ring structure defining a central opening that may be enlarged or constricted (i.e., made smaller) by mechanical adjustment, e.g., via application of force to opposing surfaces at the opening of the ring. FIG. 4C illustrates another exemplary embodiment in which mechanical force, exerted by deformation of the reservoir 115 and/or the valve body 105, is utilized to seal the aperture 110. The deformation of the reservoir 115 is designed to create specific deformations at specific reservoir fill characteristics (e.g., fill percentages, fill volumes, reservoir fluid pressure), thereby adjusting the deformation of the integrated valve. When the valve body 105 is bent, either by itself or via the bending of the implantable reservoir 115, a neutral-force plane 420 is defined within the valve body 105. As shown in the example of FIG. 4C, the valve body 105 experiences a tensile force above the plane 420 and a compressive force below the plane 420. The compressive force causes the aperture 110 to close. FIGS. 4D and 4E depict an exemplary structure for ring 410, which partially encircles the valve body 105 while defining gaps 430 between sections of the ring. Such gaps 430 may be partially or completely closed via application of force that pushes the segments of ring 410 together. Ring 410 may also be advantageously utilized in combination with deformation of the reservoir 105 and/or valve body 105 to limit the compression and expansion caused by the compression and tensile forces, respectively. As shown in FIG. 4E, the ring 410 may at least partially encircle the valve body 105 at a height along the thickness of body 105 to selectively limit the forces applied (via, e.g., deformation of the valve body 105 and/or reservoir 115) at one or more particular points along the thickness of body 105, i.e., to limit the necessary closing pressure because the force is applied around only a portion of the valve body 105 rather that along its entire height. The ring 410 maintains a specific range of compressive force applied to the valve 105 while additionally multiplying the compressive force caused by any thermal expansion of the valve 105 material.

Needle Guidance and Retention Structures

In accordance with embodiments of the present invention, when a needle or other tool is inserted into the valve 100 to access the reservoir 115, a guide structure may be used to facilitate accurate insertion. In one example, as shown in FIG. 5A, the guide structure includes or consists essentially of an indentation 500 leading into the self-sealing aperture 110—i.e., the narrow aperture 110 flares out toward the open end at the top of the valve body 105. When the needle 200 reaches the indentation 500, which may be tapered (at, e.g., an angle approximately equal to an angle defined at the tip of needle 200), it is guided into the aperture 110. Another example, shown in FIG. 5B, utilizes a visible marking 505 near (e.g., at least partially encircling) the aperture 110 as a guide structure. The marking 505 may be applied to the top surface of the valve body 105 or may be a portion of valve body 105 proximate the aperture 110. The visible marking 505 may include or consist essentially of a colored ring or fluorescent ring that aids in pinpointing the location of the aperture 110. In embodiments in which the visual marking is a physical ring instead of merely pigmentation, the ring may be a denser material that extends over a portion of the top surface of the valve 105, thereby limiting needle insertion therethrough. With the visible marking 505, the needle 200 may be aligned accurately and inserted into the aperture 110 by an operator or by an automated system utilizing machine-vision systems known in the art.

As shown in FIG. 5C, embodiments of the invention may also incorporate a magnetic interlock as a guide structure for aperture 110. An insertion guide 510 encircling or partially encircling may incorporate one or more magnetic sections 515 (e.g., a magnetic ring) therein or thereon, and one or more magnetic sections 515 having an identical configuration but the opposite polarity may be disposed on or in (e.g., just below the surface of) the valve body 105. The magnetic attraction resulting when the guide 510 approaches the valve body 105 may be position the needle 200 directly above the aperture 110 so that it may conveniently be urged therethrough. The guide 510 may be a portion of a filling device that, as shown, has the form of a tube (at least at an end thereof) defining a lumen that contains the needle 200 (which may be retractable) therein. Advantageously, the embodiment of FIG. 5C (as well as those of FIGS. 5D-5F) facilitate maintaining contact between the valve body and the needle or filling device during insertion of the needle into the aperture 110; in this manner, force applied by the needle does not push the valve away from the needle before the needle can penetrate into and/or through the aperture 110.

FIG. 5D illustrates a guide structure that includes or consists essentially of a mechanical interlock. As shown, the needle 200 may incorporate (or be part of a filling device that incorporates) a guide 520 having one or more mechanical features (e.g., notches, threads, etc.) complementary to a guide 525 disposed on or in the valve body 105. One or both guides 520, 525 may include or consist essentially of, e.g., a screw, a twistlock, an inset structure, or other suitable structure. Such mechanically interlocking features may be disposed on the external portion of the valve 100 and/or disposed within a recessed portion of the valve 100. The guide 520 may be a portion of a filling device that, as shown, has the form of a tube (at least at an end thereof) defining a lumen that contains the needle 200 (which may be retractable) therein.

FIGS. 5E and 5F depicts the use of a mechanical guide tube 530 adhered to the valve body 105 by, e.g., vacuum suction, for guidance of the needle 200. When the vacuum is on, the guide tube 530 is drawn against the valve body 105 and guides the insertion needle 200 to align with the aperture 110. When the vacuum is off, the guide tube 530 may be removed from the valve body 105. At least a portion of (e.g., the end of) the guide tube 530 may be treated with a compatible polymer layer to promote adhesion and sealing to the valve body 105 when a vacuum is applied. To facilitate alignment, the guide tube 530 may include a flange 532 sized to slide snugly over the valve body 105 and, if desired, a rib 535 that rests on surface of the valve body for stability (i.e., to keep the needle 200 aligned with the aperture 110). Alternatively, an O-ring on the surface of the valve body 105 and encircling the aperture 110 may replace the rib 535 but provide the same function. The guide tube 530 may be a portion of a filling device that, as shown, has the form of a tube (at least at an end thereof) defining a lumen that contains the needle 200 (which may be retractable) therein. The vacuum may be applied through the lumen via a vacuum means (e.g., a vacuum pump) 540.

Multipart Valves

In accordance with embodiments of the invention, the valve may include or consist essentially of a single part (or "segment" or "portion") or multiple parts that are assembled together. For example, the valve body 105 may be a single unitary structure, as shown in FIGS. 1A and 1B. Valve body 105 may have any of various shapes, e.g. rectangular, cylindrical, etc., and may be formed from different materials with different properties, e.g., silicone, polymers, gels, plastics, or other biocompatible materials. In various embodiments, one or more segments of the valve are flexible (i.e., elastomeric), while one or more other segments of the valve are rigid. As utilized herein, the term "elastomeric" refers to including, consisting essentially of, or consisting essentially of one or more elastomers, and/or a material able to resume its original shape when a deforming force is removed. As utilized herein, the term "elastomer" refers to a processable polymer with glass transition temperature below room temperature, which is crosslinked after shaping via chemical crosslinking reactions. Elastomers have viscoelasticity (i.e., both viscosity and elasticity) and very weak inter-molecular forces, and thus generally have low Young's modulus and high failure strain compared with other materials. A "rigid" or "high-durometer" segment may have a durometer of greater that approximately 70 on the Shore A hardness scale and/or greater than approximately 75 on the Shore D hardness scale, while "flexible" or "low-durometer" segments may have smaller hardnesses. Typically, rigid segments and materials are not puncturable by insertion or filling tools such as needles. Rigid segments may be highly or fully crosslinked or reinforced) polymer or plastic, e.g., thick layers of PDMS, polyimide, polypropylene, polyaryletheretherketone ("PEEK"), polycarbonate, acetyl film (e.g., acetyl copolymer), and/or polyoxymethylene plastic (e.g., DELRIN).

Figure 6A:
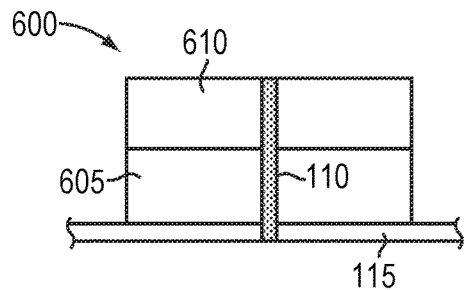
FIG. 6A is a schematic cross-sectional view of a multi-portion valve in accordance with various embodiments of the invention.
Figure 6C:
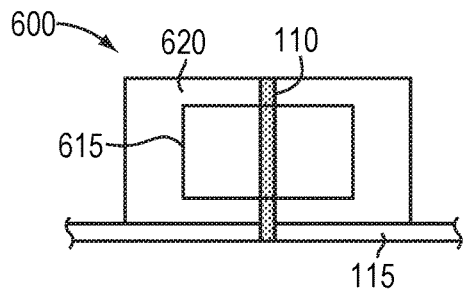
FIG. 6C is a schematic cross-sectional view of a multi-portion valve in accordance with various embodiments of the invention.
Figure 6B:
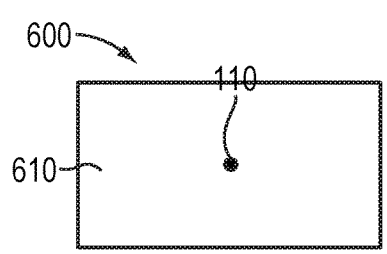
FIG. 6B is a top view of the multi-portion valve of FIG. 6A.

A valve 600 including, consisting essentially of, or consisting of multiple parts or sections, as shown in FIGS. 6A-6F, may be assembled in different configurations. As shown in FIGS. 6A and 6B, valve 600 may include, consist essentially of, or consist of two stackable portions 605, 610. This construction simplifies manufacture by enabling fabrication of differently sized valves using a single basic unit, and as discussed further below, permits use of materials with different properties affecting operation of the valve. The stacked portions may be joined using an adhesive, thermal fusion, overmolding, staged deposition, or any other suitable mechanism.

Figure 6D:
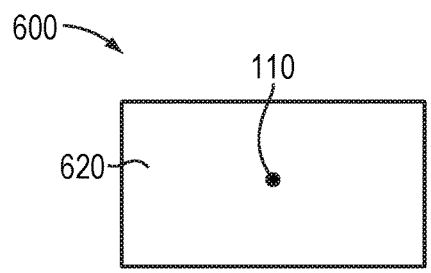
FIG. 6D is a top view of the multi-portion valve of FIG. 6C.

As shown in FIGS. 6C and 6D, valve 600 may be composed of two portions 615, 620, where portion 620 surrounds and encapsulates portion 615. For example, the portions 615, 620 may be made of different materials as detailed below. As used herein, the term "contiguous" in reference to valve portions or segments refers to constructions in which the segments are contiguous by being joined together or by encapsulation of one or more segments within one or more other segments.

Figure 6E:
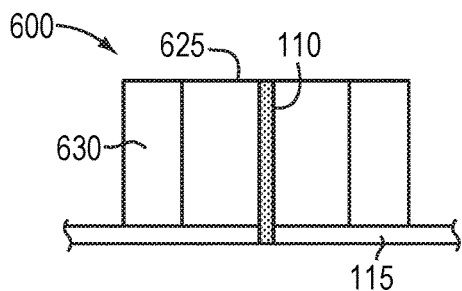
FIG. 6E is a schematic cross-sectional view of a multi-portion valve in accordance with various embodiments of the invention.
Figure 6F:
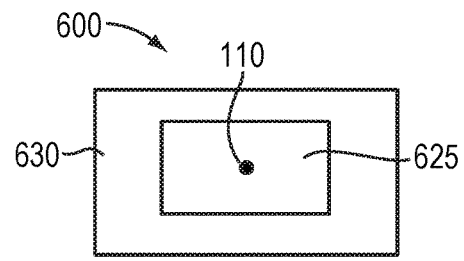
FIG. 6F is a top view of the multi-portion valve of FIG. 6E.

FIGS. 6E and 6F illustrate a valve 600 having concentric rather than stacked portions 625, 630, where portion 625 forms an interior "pillar" of the valve (within which the aperture 110 is defined) that is encircled by the annular portion 630. Like the embodiment shown in FIGS. 6A and 6B, this configuration can simplify manufacture when valves having different overall diameters or physical properties are needed. For example, the central valve portion 625 may be a standard component that may be surrounded by different annular portions 630 in order to attain a desired valve footprint or to adjust the radial sealing force applied to the central valve portion 625 (e.g., a pre-stressed annular portion 630 will permanently squeeze the central valve portion 625). The annular portion 625 may have a stepped or radially sloped design to allow for easier integration with the reservoir 115 membrane.

The various different portions of a multi-part valve (e.g., valve 600) may each include, consist essentially of, or consist of different materials and/or may have different mechanical properties. In addition, one or more portions of a multi-part valve (including valves composed of more than two portions as detailed below) may have induced preloaded axial compression to facilitate self-sealing of the aperture 110 at least in such portion(s).

Although FIGS. 6A-6D illustrate valves having two distinct sections, configurations with more than two sections may be utilized as shown in FIGS. 7A-7D, which depict various three-segment valve configurations. As shown in FIG. 7A, three portions 705, 710, 715 may be stacked in layer-by-layer fashion to form valve 700. Alternatively, as shown in FIG. 7B, a portion 720 may be surrounded by an encapsulating portion 725, which is itself surrounded by an outer encapsulating portion 730. FIG. 7C depicts a valve 700 in accordance with embodiments of the invention in which a portion 735 forms an interior pillar of the valve (within which the aperture 110 is defined) that is successively encircled by rings formed by portions 740, 745. Two or more of these approaches may be combined if desired. For example, FIG. 7D depicts a valve 700 in accordance with embodiments of the invention in which a portion 750 is surrounded by an encapsulating portion 755, which is in turn stacked atop a portion 760. Valves in accordance with embodiments of the present invention may also include or consist essentially of four or more assembled portions.

Multi-portion valves may also facilitate convenient construction of valves having different internal configurations. For example, both linear and non-linear apertures may be implemented within a single multi-portion valve. FIG. 8A depicts a multi-portion valve 800 similar to that depicted in FIG. 6A, but in which a substantially linear aperture 110 penetrates through both portions 605, 610 at an angle not normal to the top and bottom surfaces of the valve body. In the alternative structure shown in FIG. 8B, valve 800 incorporates an aperture 110 that is not completely straight, i.e., which has fluidically contiguous segments oriented at different angles; the aperture 110 extends through each of portions 605, 610 at a different angle with respect to the top surface of the valve body. In other variations, one or more aperture segments may be non-linear. FIG. 8C depicts another exemplary valve 800 featuring an angled aperture 100. As shown, the portion of the aperture 110 extending through portion 605 is oriented in one direction and the portion of the aperture 110 extending through portion 610 is bent at an angle (e.g., approximately 90°) thereto and exits the sidewall of the valve body.

Angled and/or multi-section valve apertures in accordance with various embodiments of the invention may provide higher sealing pressure than straight apertures, thus helping to prevent the contents of the implantable reservoir from leaking out. This may be further promoted by having aperture portions of different radii (or other lateral dimension, for apertures having non-circular cross-sections). When the valve is subject to stresses in certain directions, these stresses may act to either open or close the valve. In such circumstances, the orientation of the valve and/or the valve aperture with respect to the stress vectors to which the implantable reservoir is subjected may affect valve function and may be accounted for in the design. A bent valve aperture may be redundantly closed at different portions along the length of the aperture, even though closure of only a single section is required to close the valve. For example, compression along the horizontal direction causes the aperture 110 of valve 800 in FIG. 8A to close, while compression in the vertical direction would be less effective. However, vertical compression causes the horizontal portion of the aperture 110 of valve 800 in FIG. 8C to close. Likewise, a horizontal compression along the vertical portion of aperture 110 of valve 800 in FIG. 8C will also cause the valve to close. In this manner, multiple angles of incision (i.e., angles of the pre-formed aperture 110) may be used to seal over a greater range of stresses or strains encountered by the valve.

In accordance with various embodiments of the invention, multi-portion valves may advantageously be composed of portions that include, consist essentially of, or consist of materials with different properties. For example, FIG. 9 depicts an exemplary valve 900 composed of stacked portions 905, 910, 915, 920, 925, 930 and in which different portions of the valve may be either hydrophobic or hydrophilic. For example, layers 905, 915, 925 may be hydrophobic, and layers 910, 920, 930 may be hydrophilic (or vice versa), thereby improving the sealing properties of the aperture 110 to stop fluid of any polarity from leaking or diffusing out of the valve. For the valve 600 shown in FIGS. 6C and 6D, the outside encapsulation portion 620 may include, consist essentially of, or consist of a higher-durometer material to provide improved mechanical support, whereas the inside filler portion 615 may include, consist essentially of, or consist of a lower-durometer material such as a gel. As utilized herein, the term "gel" means a jelly-like colloid in which a liquid is dispersed in a solid. Gels typically recover their original configurations after being pierced by a tool such as a needle and removal of the tool from the gel. An aperture 110 through such a gel portion may be opened by the insertion of a tool such as a needle, and the aperture 110 will close again after the tool is removed. The structure of the gel may improve the self-sealing property of the valve aperture; because gels typically have low cross-linking densities, they may recover such cross-links after the tool is removed, restoring the original sealed configuration of the aperture. These layers may additionally have alignment features or interlocking mechanical structures (e.g., tabs and recesses) to further promote inter-layer adhesion.

With reference to valve 600 depicted in FIGS. 6C and 6D, in accordance with various embodiments of the invention, in such valves having an interior portion encapsulated by an outer portion, the exterior encapsulating portion 620 may include, consist essentially of, or consist of a higher-durometer material to provide improved mechanical support, while the interior portion 615 may include, consist essentially of, or consist of a drug-embedded polymer that may serve the function of short-term drug release when implemented with an implantable reservoir.

Figure 10B:
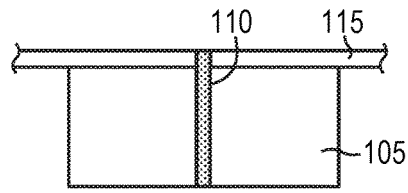
FIGS. 10A-10C are schematic cross-sectional views of valves at different locations relative to a membrane of an implantable reservoir in accordance with various embodiments of the invention.
Figure 10A:
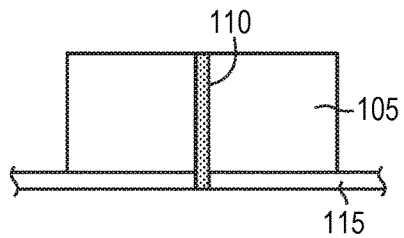
Figure 10C:
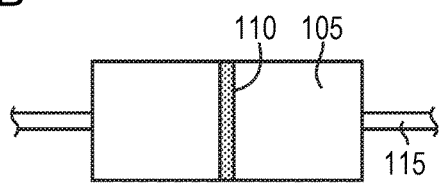

In the exemplary embodiments described above, the valves are all disposed above the membrane 115 of the implantable reservoir, as shown in FIG. 10A. In various other embodiments, the valves may be disposed in other positions relative to the reservoir, as shown in FIG. 10B (in which the valve is disposed beneath the membrane and thus within the reservoir) and 10C (in which a portion of the valve is disposed above the membrane and a portion of the valve is disposed below the membrane). Such different orientations may be advantageous in accommodating different folding patterns of unfilled implantable reservoirs.

Figure 11:
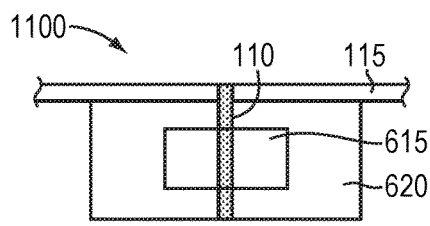
FIGS. 11-13 are schematic cross-sectional views of multi-portion valves in accordance with various embodiments of the invention.

FIG. 11 depicts an exemplary valve 1100 in accordance with embodiments of the invention in which the valve is underneath the membrane 115 of the implantable reservoir, i.e., within and facing the interior of the reservoir. The valve body has two portions, an interior portion 615 and a surrounding encapsulation portion 620. The aperture 110 is straight and passes through both portions of the valve. The aperture 110 allows an external insertion tool such as a hypodermic needle to access the interior of the reservoir and self-seals after the insertion tool is removed. In addition, the two portions of the valve 1100 may include, consist essentially of, or consist of different materials. The outside encapsulation portion 620 may include, consist essentially of, or consist of a higher-durometer material to enhance self-sealing. The inside filler portion 615 may include, consist essentially of, or consist of a polymer with an embedded or entrained pharmaceutical. After implantation of the reservoir 115, the pharmaceutical in the filler portion 615 may slowly be released into the reservoir 115 and from there be released into the implant host. Alternatively or in addition, the outer portion 620 may include an embedded or entrained pharmaceutical for better contact with and diffusion into the reservoir 115.

In various embodiments of the invention, a pharmaceutical embedded or entrained within at least a portion of the valve is released directly from the valve to the implant host, or into the reservoir for subsequent administration to the implant host. In various embodiments, the pharmaceutical is injected into the valve following implantation, either once or multiple times. In other embodiments, the valve is prefilled with a pharmaceutical. Using an encapsulated portion of the valve to contain the pharmaceutical is, in accordance with various embodiments, advantageous because the encapsulated portion may have a polarity different from that of the implant or surrounding portion(s) of the valve. For example, the pharmaceutical may be dissolved in a hydrophilic liquid, while the implant reservoir may include, consist essentially of, or consist of a hydrophobic material. If the valve portions differ in polarity or other chemical property from the pharmaceutical and the surrounding tissue, they may act to slow diffusion of the pharmaceutical to the surrounding tissue, thereby enabling an extended release. Likewise, the filling material may be a matrix bound to or entraining a pharmaceutical for extended release. Because the mechanical or chemical properties of the pharmaceutical-containing layer may not be ideal for the structure of the entire valve or the wall of the implantable reservoir, the pharmaceutical layer may be encapsulated by one or more other portions of the valve or the pharmaceutical may be included only in a portion of a stacked valve configuration as illustrated in FIG. 9, e.g., in one or more of the stacked disks or portions 905, 910, 915 in varying concentrations (or the same concentration). Two-stage elution processes may be altered to precisely control drug delivery and/or create varying gradients of drug concentrations over time. Many medicaments may be used, e.g., antibiotics to prevent infection, steroids to facilitate healing of surrounding tissue, anti-growth factors or anti-fibrosis factors to control growth of surrounding cells, or other medicaments that may be beneficial for surrounding tissue.

Figure 12:
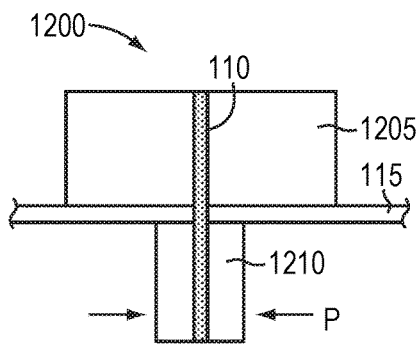

FIG. 12 illustrates another valve configuration 1200 in accordance with embodiments of the present invention. As shown, valve 1200 has two portions 1205, 1210, one of which is above the membrane 115 (i.e., outside the reservoir) and the other of which is underneath the membrane 115 (i.e., within the reservoir). The outside portion 1205 of the valve may include, consist essentially of, or consist of a higher-durometer (i.e., high hardness or high resistance to permanent deformation) material and have a larger size for easier access by an external insertion tool. The outside portion 1205 may be rigid. The inside portion 1210 may include, consist essentially of, or consist of a lower-durometer material and be smaller in size, so that the inside portion 1210 is easier to deform. The inside portion 1210 may be flexible (i.e., elastomeric). For an implantable reservoir, the pressure inside the reservoir 115 helps to compress the inside portion 1210 of the valve 1200 and helps to enhance the self-sealing properties of the aperture 110. For example, the diameter of valve portion 1210 may be less than half the diameter of valve portion 1205, or less than one-fourth the diameter of valve portion 1205, etc. The relative diameters of the two valve portions may depend, for example, on the durometers of the different materials and the expected pressure within the reservoir.

Figure 13:
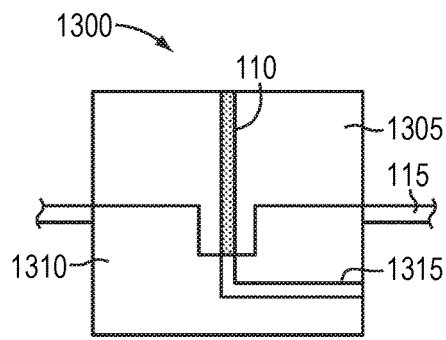

FIG. 13 depicts an exemplary multi-portion valve 1300 in accordance with embodiments of the invention. As shown, valve 1300 has two portions 1305, 1310 and is embedded into (i.e., spans) the membrane 115 of the reservoir. The self-sealing aperture 110 is disposed within the top portion 1305 of the valve 133, which, in various embodiments, includes, consists essentially of, or consists of an elastomeric material. The bottom portion 1310 of the valve 1300 may be more rigid and act as a self-stopper when an external insertion tool such as hypodermic needle is used to access the aperture 110; the needle will be stopped when it reaches the rigid bottom portion 1310 of the valve 1300. As shown, valve 1300 also features a normally open tunnel 1315 in the bottom portion 1310 that is aligned with and fluidly connected to the aperture 110. Therefore, when an insertion tool such as a hypodermic needle reaches the bottom portion 1310 of the valve 1300, the needle may inject or retrieve the contents inside the implantable reservoir through the tunnel 1315. For example, the needle exit opening may have a larger diameter than that of the tunnel 1315, so that the rigid bottom portion 1310 acts as a floor to prevent further ingress of the needle but does not prevent fluid communication between the needle lumen and the reservoir via the tunnel 1315; the needle exit opening remains aligned with the tunnel 1315 due to the height of the aperture 110 and the surrounding bulk of the top portion 1305. After the needle is removed, the self-sealing aperture 110 in the top portion 1305 of the valve 1300 will close and prevent the leakage of the contents of the reservoir. The bottom portion 1310 may additionally include, consist essentially of, or consist of a filter component (e.g., platinum mesh, polymer lattice, etc.) on the distal surface to needle entry to filter any unwanted particles (e.g., debris, large drug coagulations, etc.) that may otherwise be introduced into the reservoir. Such filtered material may be evacuated during subsequent removal of fluid from the reservoir. Such a filter component or filtering function may be integrated in one or more layers of a stacked valve as previously described with respect to FIG. 9.

Methods of Manufacture

Figure 14A:
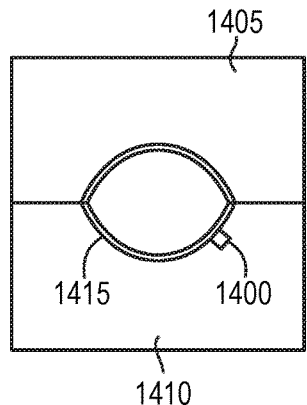
FIGS. 14A-14C schematically depict the fabrication of implantable reservoirs having valves in different configurations in accordance with various embodiments of the invention.
Figure 14B:
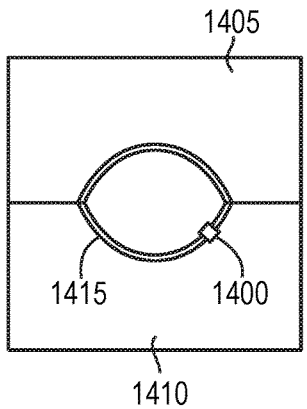
Figure 14C:
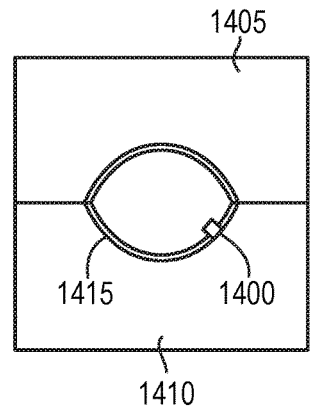

As depicted in FIGS. 14A-14C, a self-sealing valve 1400 may be attached to an implantable reservoir in various different configurations. Attachment of the valve 1400 may occur during or after manufacture of the implantable reservoir. In an exemplary embodiment, a balloon-type intraocular lens may be fabricated by coating two sections 1405, 1410 of a mold with an uncured polymer 1415, fastening the two halves 1405, 1410 together, and curing the polymer 1415 by, e.g., heating the mold, exposing it to actinic radiation, or other curing mechanism. Upon curing and opening the two halves 1405, 1410, a closed balloon-type lens is formed. The polymer 1415 may be any curable biocompatible polymer such as, for example, parylene (poly (p-xylylene)), silicone, polyurethane, etc.

To incorporate the valve 1400, a partially cured valve 1400 may be placed in a cavity in mold half 1410 before the mold half 1410 is coated with uncured polymer. As shown in FIGS. 14A-14C, the depth of the mold cavity determines whether the valve 1400 is located outside of the reservoir (FIG. 14A), partially inside the reservoir (FIG. 14B), or outside the reservoir (FIG. 14C) in the final device. The valve is coated along with the mold half 1410, the two coated mold halves 1405, 1410 are joined, and the polymer is cured. Upon opening the mold halves 1405, 1410, a balloon intraocular lens incorporating valve 1400 is formed. Final curing of the reservoir and the valve 1400 may result in cross-linking or other covalent bonding between the valve 1400 and the surrounding reservoir layer, because the partially cured valve 1400 may still have uncured/unbonded functional groups available for chemical bonding. Upon further curing, the unbonded functional groups bond with the uncured polymer.

In various embodiments of the invention, the valve is manufactured while attached to the implantable reservoir. For example, portions of a layered valve may be fused to the side of the reservoir originally manufactured with a single valve layer. Subsequent layers may be added and cured onto the device as it is formed in situ.

Another manufacturing technique in accordance with embodiments of the invention involves placing the valve on the reservoir in two portions. The first portion of the valve is placed on the mold cavity and then coated with the wall of the implantable reservoir, as described above. Before closing the reservoir, the second portion of the valve is placed on the first portion of the valve. This second valve portion protrudes into the reservoir, as shown in, e.g., FIG. 12. The two valve portions are bonded together either with a separate glue/epoxy material, or are joined by the coating (i.e., reservoir) material. After curing, portions of the valve are located both inside and outside the reservoir. In such embodiments, the two portions of the valve may be held together with an interlocking device. As described above, the valve portions may be partially cured before being cured together into a final valve that is fused with the wall of the reservoir.

Figure 15A:
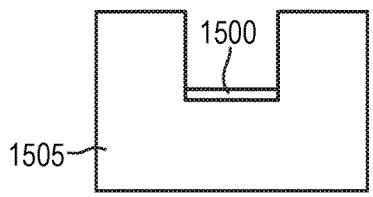
FIGS. 15A-15C schematically depict the fabrication of a multi-portion valve in accordance with various embodiments of the invention.
Figure 15B:
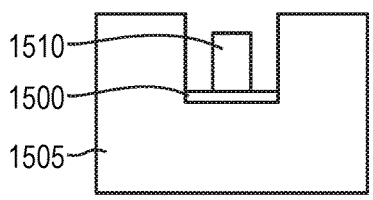
Figure 15C:
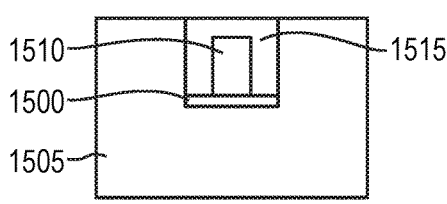

In various embodiments of the invention, self-sealing valves are fabricated before mounting to the reservoir. For example, the valve shown in FIG. 11 may be constructed by first disposing a bottom portion 1500 of the valve into a valve mold 1505, as shown in FIG. 15A. Then a middle portion 1510 of the valve is placed on the bottom portion 1500 (as shown in FIG. 15B), and finally the top portion 1515 of the valve is added (as shown in FIG. 15C), resulting in the final multi-portion valve. The various portions of the valve may be at least partially cured before the subsequent portions are added. After valve manufacture, the valve may be fastened to the reservoir. In such embodiments, the final curing of the valve may occur after attachment to the reservoir as described above.

Benefits of a Flexible Valve for an Inflatable Intraocular Lens

As mentioned above, a flexible sealing valve may be beneficial for an implantable reservoir (or "implant") that is itself flexible. This prevents a portion of the implant (i.e., where the valve is) from being stiff while the other portions of the implant are flexible. Such a mismatch between mechanical properties of the valve and surrounding implant may cause areas of high stress concentration, and hence failure. If the implant is collapsible, for example, in the case of a calf or breast implant filled after implantation, a stiff valve may not be compatible with folding of the device during insertion. Likewise, a stiff valve may cause unwanted local deformation of the implant, leading to undesired shape of the implant.

When a flexible valve is used for an inflatable intraocular lens, the flexibility assists during insertion through small surgical incisions. Preferably these incisions are smaller than 3 mm. Therefore, to fit the device through the insertion, the intraocular lens is typically compressed or deformed. A stiff valve going through the inserter may push against surrounding portions of the intraocular lens, causing high levels of pressure and friction against the wall, and shearing of the intraocular lens during implantation.

After implantation, an inflatable intraocular lens fills out a specific shape, which may be determined in part by the amount of filling. However, as filling occurs, the walls of the implant expand and flex. A uniform flexing is desired in many intraocular lens implants to maintain a good optic quality. A rigid valve may cause local deformation of the surrounding lens, which in turn may cause local non-uniformities of the lens surface and reduced optical performance.

Figure 16:
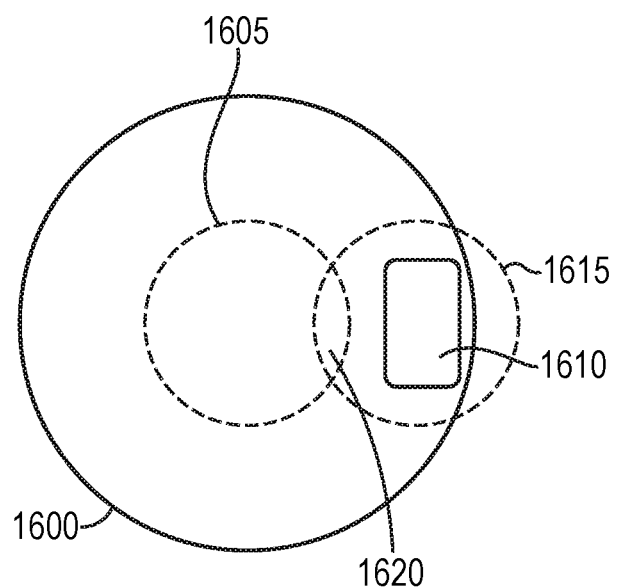
FIG. 16 is a schematic illustration of an implantable fillable intraocular lens in accordance with various embodiments of the invention.

FIG. 16 schematically illustrates an inflatable intraocular lens 1600, the central portion of which is the optical portion 1605 of the lens—i.e., the portion of the lens used for imaging. This area typically corresponds to the pupil size of the patient. The pupil size may vary between approximately 3 mm and approximately 9 mm, depending on lighting conditions (with low lighting having a larger diameter) and person-to-person variation. For reference, in current intraocular lens ISO standards, the minimum optic diameter is 4.25 mm.

The valve 1610 of the inflatable implant 1600 may be placed on the periphery of the lens, peripheral to the optical portion 1605. Around the valve 1610 is an locally deformed area 1615 of the lens surface, the deformation of which is based on the size and flexibility of the valve 1610. If this region 1615 of local deformation crosses into the optical portion 1605 of the lens, it may deform an area 1620 of the optical portion 1605, causing reduction in overall lens quality and reduced visual acuity. Therefore, embodiments of the present invention feature flexible self-sealing valves of sufficient flexibility and/or located sufficiently far from the optical portion of an intraocular lens such that the optical portion of the lens is substantially free of distortion caused by the valve.

The terms and expressions employed herein are used as terms and expressions of description and not of limitation, and there is no intention, in the use of such terms and expressions, of excluding any equivalents of the features shown and described or portions thereof. In addition, having described certain embodiments of the invention, it will be apparent to those of ordinary skill in the art that other embodiments incorporating the concepts disclosed herein may be used without departing from the spirit and scope of the invention. Accordingly, the described embodiments are to be considered in all respects as only illustrative and not restrictive.

What is claimed is:

1. An inflatable intraocular lens (IOL) implantable in a human eye, the intraocular lens including a reservoir configured to receive an optically clear filling fluid and expand in response thereto, the reservoir comprising:
   a flexible membrane defining an interior volume; and
   a self-sealing valve integrated with the membrane, the valve comprising (i) a plurality of contiguous polymeric segments and (ii) a pre-formed aperture extending through at least one of the segments and into the interior volume,
   wherein a first portion of the valve is disposed outside of the interior volume, and a second portion of the valve is disposed within the interior volume,
   wherein the aperture is normally closed to prevent fluid flow therethrough but is openable in response to applied pressure from a blunt needle passing through to an interior of the intraocular lens in order to fill or adjust the optically clear fluid within the reservoir, wherein at least one of the segments has a physical or chemical property affecting self-sealing of the aperture that differs from that of at least one of the other contiguous segments, wherein a first one of the segments surrounds and fully encapsulates a second one of the segments, the preformed aperture extending through both the first and second ones of the segments, wherein the first one of the segments is made of a higher durometer material to provide improved mechanical support and to enhance self-sealing, wherein the second one of the segments comprises a pharmaceutical agent disposed therewithin and is made of a lower durometer material to provide short-term release of said pharmaceutical agent, and wherein the valve is deformable, whereby, in response to fluid pressure within the interior volume, a portion of the aperture experiences compressive force acting to close the aperture.

2. The intraocular lens (IOL) of claim 1, wherein (i) a first portion of the aperture extends along a first direction through one of the segments, and (ii) a second portion of the aperture extends along a second direction through another one of the segments, the second direction being different from the first direction.

3. The intraocular lens (IOL) of claim 1, wherein at least two of the segments have different polarities, whereby the at least two of the segments function as a diffusion barrier.

4. The intraocular lens (IOL) of claim 1, wherein the membrane defines said intraocular lens.

5. The intraocular lens (IOL) of claim 1, wherein a diameter of the first portion of the valve is greater than a diameter of the second portion of the valve.

6. The intraocular lens (IOL) of claim 1, wherein (i) the aperture extends through the first portion of the valve, and (ii) the second portion of the valve defines a normally open tunnel fluidly connected to the aperture.

7. The intraocular lens (IOL) of claim 1, wherein the valve is configured to deform in response to deformation of the flexible membrane.

8. The intraocular lens (IOL) of claim 1, wherein the valve is configured to deform in response to one or more fill characteristics of the reservoir.

9. The intraocular lens (IOL) of claim 8, wherein the one or more fill characteristics comprise at least one of fill percentage, fill volume, or reservoir fluid pressure.

10. The intraocular lens (IOL) of claim 1, wherein the valve defines a recessed indentation leading into the aperture.

11. The intraocular lens (IOL) of claim 1, wherein the valve is deformable, whereby, in response to fluid pressure within the interior volume, the first portion of the valve experiences tensile force.

12. The intraocular lens (IOL) of claim 1, wherein the valve is deformable, whereby, in response to fluid pressure within the interior volume, the second portion of the valve experiences compressive force acting to close the aperture.

* * * * *